United States Patent [19]

Miller et al.

[11] 4,254,261
[45] Mar. 3, 1981

[54] DEHYDROABIETYLAMMONIUM SALTS OF 6-OXO-2-PIPERIDINECARBOXYLIC ACID

[75] Inventors: Stewart M. Miller, Watchung, N.J.; John L. Smith, Minneapolis, Minn.

[73] Assignee: Merck & Co., Inc., Rahway, N.J.

[21] Appl. No.: 84,475

[22] Filed: Oct. 15, 1979

[51] Int. Cl.³ .............................. C07D 211/78
[52] U.S. Cl. ..................... 546/203; 546/243
[58] Field of Search ............ 546/242, 243, 203

[56] References Cited

U.S. PATENT DOCUMENTS

| | | | |
|---|---|---|---|
| 2,528,267 | 10/1950 | Dearborn et al. | 260/570.8 R |
| 3,959,248 | 5/1976 | Veber et al. | 260/112.5 TR |
| 4,161,600 | 7/1979 | Miller | 546/135 |

OTHER PUBLICATIONS

Greenstein, J., et al., *J. Am. Chem. Soc.*, 75, 1994 (1953).
*Chemical Abstracts*, 62: 591C (1965) [Sjoeberg, B., et al., *Arkiv Kemi*, 22 (32), 447–50 (1964)].
Gottstein, W., et al., *J. Org. Chem.*, 30, 2072–3 (1965).
Kittila, R., *Dimethylformamide Chemical Uses*, E. I. Du Pont, Wilmington, 1967, pp. VIII–IX.

*Primary Examiner*—Henry R. Jiles
*Assistant Examiner*—Richard A. Schwartz
*Attorney, Agent, or Firm*—Daniel T. Szura; Theresa Y. Cheng

[57] ABSTRACT

6-Oxo-2-piperidinecarboxylic acid has been resolved via direct crystallization of pure S-6-oxo-2-piperidinecarboxylic acid dehydroabietylammonium salt from a solvent system consisting of dimethylformamide, cyclohexane and acetone. The S-enantiomer is a required component for making certain tripeptides related to thyrotropin releasing hormone (TRH) which are central nervous system stimulants.

2 Claims, No Drawings

DEHYDROABIETYLAMMONIUM SALTS OF 6-OXO-2-PIPERIDINECARBOXYLIC ACID

BACKGROUND OF THE INVENTION

The present invention involves an improved process for resolving homopyrrolidone carboxylic acid (HPCA), i.e., 6-oxo-2-piperidinecarboxylic acid. The process allows direct and highly selective crystallization of *pure* S-HPCA dehydroabietylammonium salt [S-HPCA.DAA] from a solution containing the acid and dehydroabietylamine (DAA) in a solvent system consisting of dimethylformamide, cyclohexane and acetone.

The S-enantiomer of HPCA has been prepared via resolution of R,S-HPCA by formation of diastereomeric quinine salts followed by subsequent fractional crystallization and recovery of the individual enantiomers (U.S. application Ser. No. 753,242).

Conventionally, resolution of carboxylic acids via formation of diastereomeric salts requires (1) purification of the salts; (2) repeated fractional crystallizations with or without seeding to enrich the desired diastereoisomer; and (3) recovery of the resolved acid from the corresponding diastereoisomer salt. Very often, a different solvent is required for each step and the diminished yield after each step makes the cost of the process formidably high and industrially impractical.

The improved process of this invention is distinguishable from the conventional kinetic resolution method because it is virtually a one-step reaction-resolution process which affords a desired diastereoisomer salt without any need for fractional crystallization. The S-HPCA.DAA salt is the only diastereoisomer that crystallizes from the solvent system. Furthermore, none of the conventionally required purification of crude salts; enrichment of the desired isomer; seeding; or final purification is necessary, since the pure S-HPCA.DAA salt is directly crystallized from the crude reaction mixture. As a result, the improved resolution process is much shorter and simpler, and more economic than the conventional processes.

DETAILED DESCRIPTION OF THE INVENTION

HPCA (homopyrrolidone carboxylic acid or 6-oxo-2-piperidinecarboxylic acid) has the structural formula:

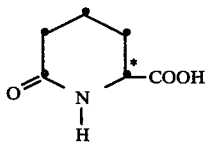

which exists as a mixture of the S-enantiomer, the R-enantiomer and the R,S-racemate. The S-enantiomer is a required component for making certain tripeptides related to thyrotropin releasing hormone (TRH) which are central nervous system stimulants as disclosed in U.S. Pat. No. 3,959,248. The R-enantiomer, obtained from the mother liquor, is a ready source for additional S-enantiomer upon racemization.

DAA (S-dehydroabietylamine) has the structural formula:

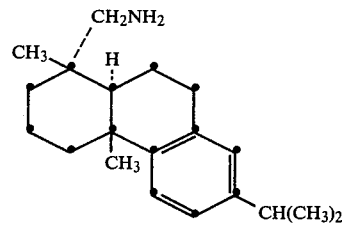

and is commercially available.

R,S-HPCA has been prepared from α-aminoadipic acid via dehydration either by pyrolysis or preferably by heating in boiling dimethylformamide.

The diastereomeric HPCA.DAA salts (R,S-HPCA.-DAA) are formed via mixing of appropriate amounts of HPCA and DAA each in an appropriate solvent. The following solvent systems have been investigated:

(1) R,S-HPCA is acetonitrile mixed with DAA in acetonitrile;

(2) R,S-HPCA in dimethylformamide mixed with DAA in diethyl ether; and (3) R,S-HPCA in dimethylformamide mixed with DAA in cyclohexane and sufficient amount of acetone to form a homogeneous system.

Both systems (1) and (2) yield the expected mixtures of diastereomeric HPCA.DAA salts. System (3), however, affords an unexpectedly high yield (up to 37% by weight; 74% by resolution) of pure S-HPCA.DAA salt, uncontaminated by any other diastereoisomers.

Isolated R,S-HPCA.DAA salts from Systems (1) and (2) as well as that recovered from the mother liquor of System (3) have been resolved to give S- and R-HPCA free acid by the following processes:

(1) A saturated solution of R,S-HPCA.DAA salts in a polar organic solvent containing 0.5%–10% 10% by volume of water, is seeded at ambient temperature to induce the selective crystallization of S-HPCA.DAA salt. Preferably, the polar solvent is acetone or acetonitrile containing 1%–5% by volume of water. Even more preferably, the polar solvent is acetone containing 5% by volume of water or acetonitrile containing 1% by volume of water.

The S-HPCA.DAA salt is converted to S-HPCA free acid via conventional methods which involve (a) treatment with a suitable strong base such as sodium hydroxide or potassium hydroxide to form the sodium or potassium salt of S-HPCA; and (b) treatment with a strong acid such as hydrochloric acid, sulfuric acid, phosphoric acid or a strong acid cation-exchange resin, for example, Dowex 50 WX4, on the hydrogen cycle to form the S-HPCA free acid.

The R-HPCA.DAA salt which is enriched in the mother liquor is converted to R-HPCA free acid employing substantially the same procedure as described above.

(2) A saturated solution of R,S-HPCA.DAA salts is obtained via refluxing the salts in a mixture of dimethylformamide, cyclohexane and sufficient acetone to homogenize the solvent system. The resulting concentration of the R,S-HPCA.DAA salts ranges from 0.05–0.1 g./ml. of the solvent. The solution is cooled to about 15° C.–25° C. to effect the cyrstallization of S-HPCA.DAA salt with or without seeding. The ratio of cyclohexane to dimethylformamide is preferably from about 2:1 to 3:1 by volume. The most satisfactory combination is where the solvent system contains 1.44 portions of dimethylformamide, 4 portions of cyclohexane, and one portion of acetone.

Conversion of the R- or S-HPCA.DAA salt obtained by this process to corrresponding free acids is substantially the same as described in process (1).

In summary, the present invention includes three related yet severable embodiments:
(1) the new R- and S-HPCA.DAA salts;
(2) an improved process for resolving R,S-6-oxo-2-piperidinecarboxylic acid (HPCA) which allows (a) the direct formation of R,S-HPCA.DAA salts in DMF-diethyl ether without isolation or purification of the crude HPCA derived from α- aminoadipic acid; and (b) the separation of the isolated diastereo-isomers in a polar solvent system containing water or a solvent system containing cyclohexane, dimethylformamide and acetone; and preferably
(3) an improved process of resolving R,S-6-oxo-2-piperidicarboxylic acid (HPCA) which comprises: (a) heating α-aminoadipic acid in dimethylformamide to form R,S-6-oxo-2-piperdinecarboxylic acid;. and (b) adding a sufficient amount of dehydroabietylamine in cyclohexane and acetone to crystallize pure S-HPCA.DAA salt.

The following examples illustrate the process of the present invention.

EXAMPLE 1

Preparation of S-6-oxo-2-piperdinecarboxylic Acid (HPCA) From Isolated R,S-HPCA Dehydroabietylamine Salt Mixture (R,S-HPCA.DAA)

Step (a): Preparation of R,S-HPCA Dehydroabietylamine Salt Mixture

Dissolve 2.2 mg. of R,S-HPCA in 1 ml. of acetonitrile at 25° C.–30° C. and add a saturated acetonitrile solution of dehydroabietylamine (DAA) containing 4.88 mg. at 30° C. On standing 30 minutes at room temperature rosettes of needles form. Collect by centrifugation, wash with acetonitrile and vacuum dry to obtain 5.8 mg. of R,S-HPCA.DAA salts, m.p. 171° C.–173° C., characteristic ir peak (NH) at 3.9 microns.

Step (b): Preparation of S-HPCA.DAA Salt

Dissolve 21.4 mg. of S-HPCA (LOD 14.75%), equivalent to 18.24 mg. or 0.127 millimole in 1.2 ml. of acetonitrile containing 1% water. Add 1.27 ml. of a 0.1 molar solution of DAA in acetonitrile. A crystalline precipitate forms immediately. Filter and wash with acetonitrile containing 1% water. Dry in vacuum to obtain 54.5 mg., m.p. 198°–199.5°, ir very similar to the R,S-HPCA.DAA salt mixture, the major difference being the shift of the NH peak at 3.9 microns (R,S-) to 2.96 microns (S-).

Seed a sample of R,S-HPCA.DAA salt in saturated solution in acetonitrile containing 1% water with S-HPCA.DAA salt at room temperature. Concentrate the mixture with a jet of nitrogen to ⅓ volume. Crystallization occurs during concentration. Centrifuge the mixture and decant the liquors. Wash the precipitate twice with acetonitrile containing 1% of water and dry in vacuum. The m.p. is 189.5° C.–195° C., characterisitic ir peak (NH) at 2.96 microns, matching the spectrum of salt prepared from S-HPCA.

Alternatively, prepare a solution of 200 mg. of R,S-HPCA.DAA salt by warming in 4.5 ml. of acetone containing 5% of water. Seed with crystals of S-HPCA.DAA salt. Filter the thick precipitate of crystals which form on cooling to room temperature, washing with acetone containing 5% of water and vacuum dry to obtain 40 mg., m.p. 191° C.–196° C., with ir matching S-HPCA.DAA salt. Recrystallization from solvent of the same composition raises the m.p. to 202° C.–204° C. (dec.). $[\alpha]_D = +20$, (c=1 in water).

Step (c): Preparation of S-HPCA

Suspend 10.65 g. of S-HCPA.DAA salt in 106.5 ml. of water and basify with 10.65 ml. of 2.5 N sodium hydroxide solution, forming a heavy precipitate of DAA. Extract the DAA with four portions of methylene chloride. Filter the aqueous solution of S-HPCA sodium salt, and convert it to the acid over a 75 ml. column of strong acid cation exchange resin on the hydrogen cycle (Dowex 50 WX4). Complete the elution with 460 ml. of water. Concentrate the acidic eluate to obtain 3.84 g. of S-HPCA as the sesquihydrate, $[\alpha]_D^{22} = +40.4$ (dry basis), (C=1.25 in 6 N hydrochloric acid).

Step (d): Preparation of R-HPCA

Evaporate mother liquors of R,S-HPCA.DAA salt solution from which S-HPCA.DAA salt has been crystallized. Dissolve 10 g. of the residue in 100 ml. of water and make alkaline with 10 ml. of 2.5 N sodium hydroxide, precipitating DAA. Remove the DAA by extraction with a total of 100 ml. of methylene chloride (portion-wise). Filter the aqueous layer of sodium salt and pass it through a 75 ml. column of strong acid cation exchanging resin on the hydrogen cycle (Dowex 50 WX4). Complete the elution with 365 ml. of water. Concentrate the eluate in vacuo to about 45.5 ml. Filter the crystals from the mother liquor and wash with the minimum amount of water. Air dry to obtain 0.48 g. of R-HPCA. $[\alpha]_D^{22} = -42.8°$ (corr. for LOD of 13.68%), ir identical with that of S-HPCA hydrate.

EXAMPLE 2

Preparation of S-6-oxo-2-piperidinecarboxylic Acid (S-HPCA) from R,S-HPCA.DAA Salts Obtained Directly from the Reaction Mixture

Step (a): Preparation of R,S-HPCA.DAA Salt Mixture from α-Aminoadipic Acid

Reflux 1 g. of R,S-α-aminoadipic acid in 10 ml. of dimethylformamide (DMF) for 20 minutes. Allow to cool and add a solution of 1.5 g. of DAA in 20 ml. of ether. Seed with crystals of R,S-HPCA.DAA salt mixture. Allow to crystallize several hours, filter, and wash with acetone containing 5% of water, and acetone. Air dry to obtain 1.49 g. of R,S-HPCA.DAA salt, m.p. 171.5°–174.5° C.

Step (b): Preparation of S-HPCA.DAA Salt

Dissolve 1 g. of the product in 26 ml. of acetone containing 5% of water at reflux. Allow to cool, seeding with S-HPCA.DAA salt. Filter the salt which precipitates, wash with acetone containing 5% of water, acetone, and air dry to obtain 0.25 g. of S-HPCA.DAA salt, m.p. 194.5°–198° C.

Step (c): Preparation of S-6-oxo-2-piperidine Carboxylic Acid (S-HPCA)

Employing substantially the same procedure as described in Example I, Step (c), S-HPCA.DAA salt is converted to optically pure S-6-oxo-2-piperidine carboxylic acid (S-HPCA).

EXAMPLE 3

Preparation of S-HPCA.DAA Directly from Mixtures of Dehydroabietylamine and R,S-HPCA in a Solvent System Containing Cyclohexane, Acetone and Dimethylformamide

Step (a): Preparation of S-HPCA.DAA from R,S-HPCA

Combine with stirring 200 ml. of cyclohexane containing 18.5 g. of dehydroabietylamine with a solution of 7.27 g. of R,S-HPCA in 72.2 ml. of dimethylformamide. Add 50 ml. of acetone to co-dissolve the solvents. Age 1.5 hours at room temperature and filter the precipitated crystals, washing with acetone. Air dry to obtain 8.0 g. (36.8%) of S-HPCA.DAA, m.p. 191°–195° C. (inserted at 160° C.) and characteristic ir peak (NH) at 2.96 microns, matching the spectrum of salt prepared from S-HPCA.

Evaporate the mother liquors in vacuo to remove acetone and cyclohexane and stir the semi-solid residue in 200 ml. of ether for one hour at room temperature. Filter and wash the precipitate with ether and air dry to obtain 6.8 g. of R,S-HPCA.DAA, m.p. 173°–176° (31.3%).

Alternatively, dissolve 10 g. of R,S-HPCA.DAA at the boiling point in a mixture of 33.4 ml. of dimethylformamide, 91.88 ml. of cyclohexane and 32.1 ml. of acetone. Filter hot into a flask preseeded with S-HPCA.DAA. Stir at room temperature for two hours, filter and wash with acetone. Air dry to obtain 2.61 g. (26.1%) of S-HPCA.DAA, m.p. 191°–194° C. (inserted at 160°).

Step (b): Preparation of S-6-oxo-2-piperidinecarboxylic Acid (S-HPCA)

Employing substantially the same procedure as described in Example 1, Step (c), S-HPCA.DAA salt is converted to optically pure S-6-oxo-2-piperidine carboxylic acid (S-HPCA).

EXAMPLE 4

Direct Resolution of R,S-6-oxo-2-piperidinecarboxylic Acid (HPCA)

Step (a): Preparation of S-HPCA.DAA from R,S-α-aminoadipic Acid

Under a slow nitrogen sweep, distil 210 ml. from a mixture of 100 g. of R,S-α-aminoadipic acid and 862 ml. of dimethylformamide. Cool under nitrogen and adjust the volume of the solution to 888.3 ml. with dimethylformamide (theoretical weight of 0.1 g. per ml.).

To 100 ml. of this solution, add 98.8 ml. of acetone and 238.5 ml. of cyclohexane containing 20.37 g. of DAA. Seed with S-HPCA.DAA and allow to stand two days. Filter and wash with a mixture of dimethylformamide/acetone/cyclohexane 1:1:2 and then with acetone to obtain 6.4 g. (21.4%) by weight; 42.8% by resolution of S-HPCA-DAA (air dried), m.p. 193.5°–196.5° C.

Step (b): Preparation of S-6-oxo-2-piperidinecarboxylic Acid (S-HPCA)

Employing substantially the same procedure as described in Example 1, Step (c), S-HPCA.DAA is converted to optically pure S-oxo-2-piperidinecarboxylic acid (S-HPCA).

What is claimed is:
1. S-6-oxo-2-piperidinecarboxylic acid dehydroabietylammonium salt.
2. R-6-oxo-2-piperidinecarboxylic acid dehydroabietylammonium salt.

* * * * *